United States Patent [19]
Powell et al.

[11] Patent Number: 6,162,630
[45] Date of Patent: Dec. 19, 2000

[54] ASP1

[75] Inventors: David J Powell, Radnor, Pa.; Christopher Southan, Bishop Stortford, United Kingdom; Conrad G Chapman, Orpington, United Kingdom; Joanne R Evans, Herts, United Kingdom

[73] Assignees: SmithKline Beecham Corporation, Philadelphia, Pa.; SmithKline Beecham plc, Middlesex, United Kingdom

[21] Appl. No.: 09/434,427

[22] Filed: Nov. 4, 1999

Related U.S. Application Data

[62] Division of application No. 08/999,723, Oct. 6, 1997, Pat. No. 6,025,180.

[30] Foreign Application Priority Data

Dec. 14, 1996 [GB] United Kingdom ............... 9626022

[51] Int. Cl.$^7$ ................ C12N 9/50; C07K 1/00
[52] U.S. Cl. ........................... 435/219; 530/350
[58] Field of Search ................. 435/219, 320.1; 536/23.2

[56] References Cited

PUBLICATIONS

Patel, S. Pharmacotherapy of cognitive impairment in Alzheimer's disease: A review. J. Geriatr. Psychiatry Neurol. 8:81–85, 1995.
Patel et al. "Pharmacotherapy of Cognitive Impairment in Alzheimer's Disease: A Review", Journal of Geriatric Psychiatry and Neurology, vol. 8, pp. 81–95 (1995).
N–GenSeq–34 Database Accession No. Q89844, Dec. 1985.
GenBank Accession No. X59754, Nov. 1991.
GenBank Accession No. M73750, Dec. 1991.
GenBank Accession No. J04443, Jan. 1995.

*Primary Examiner*—Karen Cochrane Carlson
*Assistant Examiner*—Devesh Srivastava
*Attorney, Agent, or Firm*—William T. Han; Ratner & Prestia

[57] ABSTRACT

ASP1 polypeptides and polynucleotides and methods for producing such polypeptides by recombinant techniques are disclosed. Also disclosed are methods for utilizing ASP1 polypeptides and polynucleotides in the design of protocols for the treatment of Alzheimers's Disease, cancer, and melanoma, among others, and diagnostic assays for such conditions.

3 Claims, No Drawings

ASP1

This application is a division of application Ser. No. 08/999,723, filed Oct. 6, 1997, now U.S. Pat. No. 6,025,180 which claims the benefit of U.K. Application Serial Number 9626022.9, filed Dec. 14, 1996, both of whose contents are incorporated herein by reference in their entireties.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the Aspartic Proteinase family, hereinafter referred to as ASP1. The invention also relates to inhibiting or activating the action of such polynucleotides and polypeptides.

BACKGROUND OF THE INVENTION

There are currently five known human aspartic proteases, namely pepsin, gastricsin, cathespin D, cathespin E and renin, and these have widely varying functions. Pepsin and gastricsin are involved in nutritive processes in the stomach, cathepsin D is involved in protein turnover in many cell types, and renin has the highly specific function of angiotensin production from its precursor form, angiotensinogen. The precise role of cathepsin E remains to be confirmed, although its location in some epithelial cells types has indicated a role in antigen processing. It may also be involved in certain inflammatory conditions, e.g. *Helicobacter pylori* infection in the stomach. This indicates that the Aspartic Protiase family has an established, proven history as therapeutic targets. Clearly there is a need for identification and characterization of further members of the Aspartic Proteinase family which can play a role in preventing, ameliorating or correcting dysfunctions or diseases, including, but not limited to, Alzheimers's Disease, cancer, and melanoma.

SUMMARY OF THE INVENTION

In one aspect, the invention relates to ASP1 polypeptides and recombinant materials and methods for their production. Another aspect of the invention relates to methods for using such ASP1 polypeptides and polynucleotides. Such uses include the treatment of Alzheimers's Disease, cancer, and melanoma, among others. In still another aspect, the invention relates to methods to identify agonists and antagonists using the materials provided by the invention, and treating conditions associated with ASP1 imbalance with the identified compounds. Yet another aspect of the invention relates to diagnostic assays for detecting diseases associated with inappropriate ASP1 activity or levels.

DESCRIPTION OF THE INVENTION

Definitions

The following definitions are provided to facilitate understanding of certain terms used frequently herein.

"ASP1" refers, among others, generally to a polypeptide having the amino acid sequence set forth in SEQ ID NO:2 or an allelic variant thereof.

"ASP1 activity or ASP1 polypeptide activity" or "biological activity of the ASP1 or ASP1 polypeptide" refers to the metabolic or physiologic function of said ASP1 including similar activities or improved activities or these activities with decreased undesirable side-effects. Also included are antigenic and immunogenic activities of said ASP1.

"ASP1 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as mosine. A variety of modifications has been made to DNA and RNA, thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY. von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al,. *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to ASP1 polypeptides (or ASP1 proteins). The ASP1 polypeptides include the polypeptide of SEQ ID NO:2; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within ASP1 polypeptides are polypeptides having the amino acid sequence which have at least 80% identity to the polypeptide sequence having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably ASP1 polypeptide exhibit at least one biological activity of ASP1.

The ASP1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the ASP1 polypeptides are also included in the invention. A fragment is a polypeptide having an amino acid sequence that entirely is the same as part, but not all, of the amino acid sequence of the aforementioned ASP1 polypeptides. As with ASP1 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of ASP1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of ASP1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate ASP1 activity, including those with a similar activity or an improved activity, or with a decreased undesirable activity. Also included are those that are antigenic or immunogenic in an animal, especially in a human.

Preferably, all of these polypeptide fragments retain the biological activity of the ASP1, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln, and among the basic residues Lys and Arg; or aromatic residues Phe and Tyr. Particularly preferred are variants in which several, 5–10, 1–5, or 1–2 amino acids are substituted, deleted, or added in any combination.

The ASP1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to ASP1 polynucleotides. ASP1 polynucleotides include isolated polynucleotides which encode the ASP1 polypeptides and fragments, and polynucleotides closely related thereto. More specifically, ASP1 polynucleotide of the invention include a polynucleotide comprising the nucleotide sequence contained in SEQ ID NO:1 encoding a ASP1 polypeptide of SEQ ID NO: 2, and polynucleotide having the particular sequence of SEQ ID NO:1. ASP1 polynucleotides further include a polynucleotide comprising a nucleotide sequence that has at least 80% identity over its entire length to a nucleotide sequence encoding the ASP1 polypeptide of SEQ ID NO:2, and a polynucleotide comprising a nucleotide sequence that is at least 80% identical to of SEQ ID NO:1 over its entire length. In this regard, polynucleotides at least 90% identical are particularly preferred and those with at least 95% are especially preferred. Furthermore, those with at least 97% are highly preferred and those with at least 98–99% are most highly preferred, with at least 99% being the most preferred. Also included under ASP1 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such ASP1 polynucleotides.

ASP1 of the invention is structural red to other proteins of the Aspartic Proteinase family, as shown by the results of sequencing the cDNA of Table 1 (SEQ ID NO:1) encoding human ASP1. The cDNA sequence of SEQ ID NO:1 contains an open reading frame (nucleotide number 91 to 1644) encoding a polypeptide of 518 amino acids of SEQ ID NO:2. The amino acid sequence of Table 2 (SEQ ID NO:2) has about 50% identity (using FASTA(GCG)) in 445 amino acid residues with ASP2 Novel Aspartic Proteinase (UK Pat. Refs 9618966.7, 9618966.6 and 9618963.4). Furthermore, human 4progastricsin is 33.5% identical to ASP1 over 239 amino acid residues (Taggart, R. T. et al., J. Biol. Chem. 264:375–379, 1989). The nucleotide sequence of Table 1 (SEQ ID NO:1) has about 60.4% identity (using FASTA (GCG)) in 1347 nucleotide residues with ASP2 Novel Aspartic Proteinase (UK Pat. Refs. 9618966.7, 9618966.6 and 9618963.4). Furthermore, human progastricsin is 45% identical to ASP1 over 1385 nucleotide base residues (Taggart et al., J. Biol. Chem. 264:375–379, 1989). Thus, ASP1 polypeptides and polynucleotides of the present invention are expected to have, inter alia, similar biological functions/properties to their homologous polypeptides and polynucleotides, and their utility is obvious to anyone skilled in the art.

TABLE 1[a]

GGCCGCTGAATGGCCGAGTCGCTGAGCCGCGGCTGCCGGACGGGACGGGA

CCGGCTAGGCTGGGCGCGCCCCCGGGCCCCGCCGTGGGCATGGGCGCAC

TGGCCCGGGCGCTGCTGCTGCCTCTGCTGGCCCAGTGGCTCCTGCGCGCC

GCCCCGGAGCTGGCCCCCGCGCCCTTCACGCTGCCCCTCCGGGTGGCCGC

GGCCACGAACCGCGTAGTTGCGCCCACCCCGGGACCCGGGACCCCTGCCG

AGCGCCACGCCGACGGCTTGGCGCTCGCCCTGGAGCCTGCCCTGGCGTCC

CCCGCGGGCGCCGCCAACTTCTTGGCCATGGTAGACAACCTGCAGGGGA

CTCTGGCCGCGGCTACTACCTGGAGATGCTGATCGGGACCCCCCCGCAGA

AGCTACAGATTCTCGTTGACACTGGAAGCAGTAACTTTGCCGTGGCAGGA

ACCCCGCACTCCTACATAGACACGTACTTTGACACAGAGAGGTCTAGCAC

ATACCGCTCCAAGGGCTTTGACGTCACAGTGAAGTACACACAAGGAAGCT

TABLE 1ᵃ-continued

```
GGACGGGCTTCGTTGGGGAAGACCTCGTCACCATCCCCAAAGGCTTCAAT

ACTTCTTTTCTTGTCAACATTGCCACTATTTTTGAATCAGAGAATTTCTT

TTTGCCTGGGATTAAATGGAATGGAATACTTGGCCTAGCTTATGCCACAC

TTGCCAAGCCATCAAGTTCTCTGGAGACCTTCTTCGACTCCCTGGTGACA

CAAGCAAACATCCCCAACGTTTTCTCCATGCAGATGTGTGGAGCCGGCTT

GCCCGTTGCTGGATCTGGGACCAACGGAGGTAGTCTTGTCTTGGGTGGAA

TTGAACCAAGTTTGTATAAAGGAGACATCTGGTATACCCCTATTAAGGAA

GAGTGGTACTACCAGATAGAAATTCTGAAATTGGAAATTGGAGGCCAAAG

CCTTAATCTGGACTGCAGAGAGTATAACGCAGACAAGGCCATCGTGGACA

GTGGCACCACGCTGCTGCGCCTGCCCCAGAAGGTGTTTGATGCGGTGGTG

GAAGCTGTGGCCCGCGCATCTCTGATTCCAGAATTCTCTGATGGTTTCTG

GACTGGGTCCCAGCTGGCGTGCTGGACGAATTCGGAAACACCTTGGTCTT

ACTTCCCTAAAATCTCCATCTACCTGAGAGACGAGAACTCCAGCAGGTCA

TTCCGTATCACAATCCTGCCTCAGCTTTACATTCAGCCCATGATGGGGGC

CGGCCTGAATTATGAATGTTACCGATTCGGCATTTCCCCATCCACAAATG

CGCTGGTGATCGGTGCCACGGTGATGGAGGGCTTCTACGTCATCTTCGAC

AGAGCCCAGAAGAGGGTGGGCTTCGCAGCGAGCCCCTGTGCAGAAATTGC

AGGTGCTGCAGTGTCTGAAATTTCCGGGCCTTTCTCAACAGAGGATGTAG

CCAGCAACTGTGTCCCCGCTCAGTCTTTGAGCGAGCCCATTTTGTGGATT

GTGTCCTATGCGCTCATGAGCGTCTGTGGAGCCATCCTCCTTGTCTTAAT

CGTCCTGCTGCTGCTGCCGTTCCGGTGTCAGCGTCGCCCCCGTGACCCTG

AGGTCGTCAATGATGAGTCCTCTCTGGTCAGACATCGCTGGAAATGAATA

GCCAGGCCTGACCTCAAGCAACCATGAACTCAGCTATTAAGAAAATCACA

TTTCCAGGGCAGCAGCCGGGATCGATGGTGGCGCTTTCTCCTGTGCCCAC

CCGTCTTCAATCTCTGTTCTGCTCCCAGATGCCTTCTAGATTCACTGTCT

TTTGATTCTTGATTTTCAAGCTTTCAAATCCTCCCTACTTCCAAGAAAAA

AAAAAAAAAAA
```

ᵃA nucleotide sequence of a human ASP1 (SEQ ID NO: 1).

TABLE 2ᵇ

```
MGALARALLLPLLAQWLLRAAPELAPAPFTLPLRVAAATNRVVAPTPGPG

TPAERHADGLALALEPALASPAGAANFLAVVDNLQGDSGRGYYLENLIGT

PPQKLQILVDTGSSNFAVAGTPHSYIDTYFDTERSSTYRSKGFDVTVKYT

QGSWTGFVGEDLVTIPKGFNTSFLVNIATIFESENFFLPGIKWNGILGLA

YATLAKPSSSLETFFDSLVTQANIPNVFSMQMCGAGLPVAGSGTNGGSLV

LGGIEPSLYKGDIWYTPIKEEWYYQIEILKLEIGGQSLNLDCREYNADKA

IVDSGTTLLRLPQKVFDAVVEAVARASLIPEFSDGFWTGSQLACWTNSET

PWSYFPKISIYLRDENSSRSFRITILPQLYIQPMMGAGLNYECYRFGISP

STNALVIGATVMEGFYVIFDPAQKRVGFAASPCAEIAGAAVSEISGPFST
```

TABLE 2ᵇ-continued

```
EDVASNCVPAQSLSEPILWIVSYALMSVCGAILLVLIVLLLLPFRCQRRP

RDPEVVNDESSLVRHRWK
```

ᵇAn amino acid sequence of a human ASP1 (SEQ ID NO: 2).

One polynucleotide of the present invention encoding ASP1 may be obtained using standard cloning and screening, from a cDNA library derived from mRNA in cells of human Melanocyte, melanoma, endothelial cells, adult brain, and fibroblasts using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding ASP1 polypeptide of SEQ ID NO:2 may be identical to the polypeptide encoding sequence contained in Table 1 (nucleotide number 91 to 1644 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of ASP1 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain noncoding 5' and 3' sequences, such as transcribed, non-translated sequences, splicing and polyadenylation signals, ribosome binding sites and sequences that stabilize mRNA.

Further preferred embodiments are polynucleotides encoding ASP1 variants comprise the amino acid sequence ASP1 polypeptide of Table 2 (SEQ ID NO:2) in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding ASP1 polypeptide and to isolate cDNA and genomic clones of other genes (including genes encoding homologs and orthologs from species other than human) that have a high sequence similarity to the ASP1 gene. Such hybridization techniques are known to those of skill in the art. Typically these nucleotide sequences are 80% identical preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding ASP1 polypeptide, including homologs and orthologs from species other than human, comprises the steps of screening an appropriate library under stingent hybridization conditions with a labeled probe having the SEQ ID NO:1 or a fragment thereof, and isolating full-length cDNA and genomic clones containing said polynucleotide sequence. Thus in another aspect, ASP1 polynucleotides of the present invention further include a nucleotide sequence comprising a nucleotide sequence that hybridize under stringent condition to a nucleotide sequence having SEQ ID NO:1 or a fragment thereof. Also included with ASP1 polypeptides are polypeptide comprising amino acid sequence encoded by nucleotide sequence obtained by the above hybridization condition. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorables viruses and retroviruses, and vectors derived from combinations thereof, such as those derived from plasmid and bacteriophage genetic elements, such as cosmids and phagenids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the ASP1 polypeptide is to be expressed for use in screening assays, generally, it is preferred that the polypeptide be produced at the surface of the cell. In this event, the cells may be harvested prior to use in the screening assay. If the ASP1 polypeptide is secreted into the medium, the medium can be recovered in order to recover and purify the polypeptide; if produced intracellularly, the cells must first be lysed before the polypeptide is recovered.

ASP1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of ASP1 polynucleotides for use as diagnostic reagents. Detection of a mutated form of an ASP1 gene associated with a dysfunction will provide a diagnostic tool that can add to or define a diagnosis of a disease or susceptibility to a disease which results from under-expression, over-expression, or altered expression of ASP1. Individuals carrying mutations in the ASP1 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled ASP1 nucleotide sequences. Perfectly matched sequences can be distinguished from mismatched duplexes by RNase digestion or by differences in melting temperatures. DNA sequence differences may also be detected by alterations in electrophoretic mobility of DNA fagments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising ASP1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to Alzheimers's Disease, cancer, and melanoma through detection of mutation in the ASP1 gene by the methods described.

In addition, Alzheimers's Disease, cancer, and melanoma can be diagnosed by methods comprising determining from a sample derived from a subject an abnormally decreased or increased level of ASP1 polypeptide or ASP1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an ASP1 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly Alzheimers's Disease, cancer, and melanoma, which comprises:

(a) a ASP1 polynucleotide, preferably the nucleotide sequence of SEQ ID NO: 1, or a fragment thereof;

(b) a nucleotide sequence complementary to that of (a);

(c) a ASP1 polypeptide, preferably the polypeptide of SEQ ID NO: 2, or a fragment thereof; or (d) an antibody to a ASP1 polypeptide, preferably to the polypeptide of SEQ ID NO: 2. It will be appreciated that in any such hit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The chromosomal localization of ASP1 has been identified as 21q22 (Down's Critical Region) by radiation hybridization mapping.

Antibodies

The polypeptides of the invention or their fragments or analogs thereof, or cells expressing them can also be used as immunogens to produce antibodies immunospecific for the ASP1 polypeptides. The term "immunospecific" means that the antibodies have substantially greater affinity for the polypeptides of the invention than their affinity for other related polypeptides in the prior art.

Antibodies generated against the ASP1 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., *MONOCLONAL ANTIBODIES AND CANCER THERAPY*, pp. 77–96, Alan R Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against ASP1 polypeptides may also be employed to treat Alzheimers's Disease, cancer, and melanoma, among others.

Vaccines

Another aspect of the invention relates to a method for inducing an immunological response in a mammal which comprises inoculating the mammal with ASP1 polypeptide, or a fragment thereof, adequate to produce antibody and/or T cell immune response to protect said animal from Alzheimers's Disease, cancer, and melanoma, among others. Yet another aspect of the invention relates to a method of inducing immunological response in a mammal which comprises delivering ASP1 polypeptides via a vector directing expression of ASP1 polynucleotides in vivo in order to induce such an immunological response to produce antibody to protect said animal from diseases.

Further aspect of the invention relates to an immunological/vaccine formulation (composition) which, when introduced into a mammalian host, induces an immunological response in that mammal to an ASP1 polypeptide wherein the composition comprises an ASP1 polypeptide or ASP1 gene. The vaccine formulation may further comprise a suitable carrier. Since ASP1 polypeptides may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The ASP1 polypeptide of the present invention may be employed in a screening process for compounds which activate (agonists) or inhibit activation of (antagonists, or otherwise called inhibitors) the ASP1 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, receptors, enzymes, etc., as the case may be, of the polypeptide of the present invention; or may be structural or functional mimetics of the polypeptide of the present invention. See Coligan et al., *Current Protocols in Immunology* 1(2): Chapter 5 (1991).

ASP1 polypeptides are responsible for many biological functions, including many pathologies. Accordingly, it is desirous to find compounds and drugs which stimulate ASP1 polypeptides on the one hand and which can inhibit the function of ASP1 polypeptides on the other hand. In general, agonists are employed for therapeutic and prophylactic purposes for such conditions as Alzheimers's Disease, cancer, and melanoma. Antagonists may be employed for a variety of therapeutic and prophylactic purposes for such conditions as Alzheimers's Disease, cancer, and melanoma.

In general, such screening procedures may involve using appropriate cells which express the ASP1 polypeptide or respond to ASP1 polypeptide of the present invention. Such cells include cells from mammals, yeast, Drosophila or *E coli*. Cells which express the ASP1 polypeptide (or cell membrane containing the expressed polypeptide) or respond to ASP1 polypeptide are then contacted with a test compound to observe binding, or stimulation or inhibition of a functional response. The ability of the cells which were contacted with the candidate compounds is compared with the same cells which were not contacted for ASP1 activity.

All aspartic proteinases are inhibited by pepstatin.

The assays may simply test binding of a candidate compound wherein adherence to the cells bearing the ASP1 polypeptide is detected by means of a label directly or indirectly associated with the candidate compound or in an assay involving competition with a labeled competitor. Further, these assays may test whether the candidate compound results in a signal generated by activation of the ASP1 polypeptide, using detection systems appropriate to the cells bearing the ASP1 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a ASP1 polypeptide to form a mixture, measuring ASP1 activity in the mixture, and comparing the ASP1 activity of the mixture to a standard.

The ASP1 cDNA, protein and antibodies to the protein may also be used to configure assays for detecting the effect of added compounds on the production of ASP1 mRNA and protein in cells. For example, an ELISA may be constructed for measuring secreted or cell associated levels of ASP1 protein using monoclonal and polyclonal antibodies by standard methods known in the art, and this can be used to discover agents which may inhibit or enhance the production of ASP1 (also called antagonist or agonist, respectively) from suitably manipulated cells or tissues.

The ASP1 protein may be used to identify membrane bound or soluble receptors, if any, through standard receptor binding techniques known in the art. These include, but are not limited to, ligand binding and crosslinking assays in which the ASP1 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of ASP1 which compete with the binding of ASP1 to its receptors, if any. Standard methods for conducting screening assays are well understood in the art.

Examples of potential ASP1 polypeptide antagonists include antibodies or, in some cases, oligonucleotides or proteins which are closely related to the ligands, substrates, receptors, enzymes, etc., as the case may be, of the ASP1 polypeptide, e.g., a fragment of the ligands, substrates, receptors, enzymes, etc.; or small molecules which bind to the polypetide of the present invention but do not elicit a response, so that the activity of the polypeptide is prevented.

Thus in another aspect, the present invention relates to a screening kit for identifying agonists, antagonists, ligands, receptors, substrates, enzymes, etc. for ASP1 polypeptides; or compounds which decrease or enhance the production of ASP1 polypeptides, which comprises:

(a) an ASP1 polypeptide, preferably that of SEQ ID NO:2;

(b) a recombinant cell expressing an ASP1 polypeptide, preferably that of SEQ ID NO:2;

(c) a cell membrane expressing an ASP1 polypeptide; preferably that of SEQ ID NO: 2; or (d) antibody to an ASP1 polypeptide, preferably that of SEQ ID NO: 2. It will be appreciated that in any such kit, (a), (b), (c) or (d) may comprise a substantial component.

Prophylactic and Therapeutic Methods

This invention provides methods of treating abnormal conditions such as Alzheimers's Disease, cancer, and melanoma, related to both an excess of and insufficient amounts of ASP1 polypeptide activity.

If the activity of ASP1 polypeptide is in excess, several approaches are available. One approach comprises administering to a subject an inhibitor compound (antagonist) as hereinabove described along with a pharmaceutically acceptable carrier in an amount effective to inhibit the function of the ASP1 polypeptide, such as, for example, by blocking the binding of ligands, substrates, receptors, enzymes, etc., or by inhibiting a second signal, and thereby alleviating the abnormal condition. In another approach, soluble forms of ASP1 polypeptides still capable of binding the ligand, substrate, enzymes, receptors, etc. in competition with endogenous ASP1 polypeptides may be administered. Typical embodiments of such competitors comprise fragments of the ASP1 polypeptide.

In still another approach, expression of the gene encoding endogenous ASP1 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of ASP1 and its activity, several approaches are also available. One approach comprises administering to a subject a therapeutically effective amount of a compound which activtes ASP1 polypeptide, i.e., an agonist as described above, in combination with a pharmaceutically acceptable carrier, to thereby alleviate the abnormal condition. Alternatively, gene therapy may be employed to effect the endogenous production of ASP1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of ASP1 polypeptides in combination with a suitable pharmaceutical carrier.

Formulation and Administration

Peptides, such as the soluble form of ASP1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Nucleotides 1–285 of the full length ASP1 sequence were isolated from human melanoma Marathon-Ready™ cDNA, available from Clontech Laboratories Inc. (Palo Alto, Calif. USA). Marathon-Ready™ cDNAs are essentially cDNA libraries which have oligonucleotide adaptors ligated onto their ends. This allows the researcher to perform RACE (rapid amplification of cDNA ends) PCR using two primers, one complementary to a region of known sequence in the gene of interest and the other complementary to the ligated adaptor; resulting in an extension to the known gene sequence. RACE PCR can be performed at either the 5' or the 3' end of the gene. In this case, RACE PCR was performed on the 5' end.

Due to the very high GC content of the 5' end of the ASP1 gene it was found necessary to use the Advantage-GC™ cDNA PCR kit from Clontech for performing the PCR. It was also found necessary to use nested PCR—this is a second PCR which uses primers internal to the first pair and uses the first PCR product as a template.

The final PCR product was subcloned into the p Target™ vector, from Clontech, for DNA sequencing.

Nucleotides 286–1862 have been collated from the sequencing of available Expressed Sequence Tags (ESTs). A full length clone was obtained by ligating the RACE PCR fragment to an overlapping EST sequence.

All publications, including but not limited to patents and patent applications, cited in this specification are herein incorporated by reference as if each individual publication were specifically and individually indicated to be incorporated by reference herein as though fully set forth.

What is claimed is:

1. An isolated polypeptide comprising an amino acid sequence which is at least 80% identical to the amino acid sequence of SEQ ID NO:2 over its entire length, said polypeptide having aspartic protease activity.

2. An isolated polypeptide comprising the amino acid sequence of SEQ ID NO: 2.

3. An isolated polypeptide consisting of the amino acid sequence of SEQ ID NO: 2.

* * * * *

SEQUENCE LISTING

<160> NUMBER OF SEQ ID NOS: 2

<210> SEQ ID NO 1
<211> LENGTH: 1862
<212> TYPE: DNA
<213> ORGANISM: HOMO SAPIENS

<400> SEQUENCE: 1

```
ggccgctgaa tggccgagtc gctgagccgc ggctgccgga cgggacggga ccggctaggc      60
tgggcgcgcc ccccgggccc cgccgtgggc atgggcgcac tggcccgggc gctgctgctg     120
cctctgctgg cccagtggct cctgcgcgcc gccccggagc tggcccccgc gcccttcacg     180
ctgcccctcc gggtggccgc ggccacgaac cgcgtagttg cgcccacccc gggacccggg     240
accccctgccg agcgccacgc cgacggcttg gcgctcgccc tggagcctgc cctggcgtcc     300
cccgcgggcg ccgccaactt cttggccatg gtagacaacc tgcaggggga ctctggccgc     360
ggctactacc tggagatgct gatcgggacc ccccgcaga agctacagat tctcgttgac     420
actggaagca gtaactttgc cgtggcagga accccgcact cctacataga cacgtacttt     480
gacacagaga ggtctagcac ataccgctcc aagggctttg acgtcacagt gaagtacaca     540
caaggaagct ggacgggctt cgttgggaa gacctcgtca ccatcccaa aggcttcaat      600
acttcttttc ttgtcaacat tgccactatt tttgaatcag agaatttctt tttgcctggg     660
attaaatgga atggaatact tggcctagct tatgccacac ttgccaagcc atcaagttct     720
ctggagacct tcttcgactc cctggtgaca caagcaaaca tccccaacgt tttctccatg     780
cagatgtgtg gagccggctt gcccgttgct ggatctggga ccaacggagg tagtcttgtc     840
ttgggtggaa ttgaaccaag tttgtataaa ggagacatct ggtataccc tattaaggaa     900
gagtggtact accagatgga aattctgaaa ttggaaattg gaggccaaag ccttaatctg     960
gactgcagag agtataacgc agacaaggcc atcgtggaca gtggcaccac gctgctgcgc    1020
ctgccccaga aggtgtttga tgcggtggtg gaagctgtgg cccgcgcatc tctgattcca    1080
gaattctctg atggtttctg gactgggtcc cagctggcgt gctggacgaa ttcggaaaca    1140
ccttggtctt acttccctaa aatctccatc tacctgagag acgagaactc cagcaggtca    1200
ttccgtatca caatcctgcc tcagctttac attcagccca tgatggggggc cggcctgaat    1260
tatgaatgtt accgattcgg catttcccca tccacaaatg cgctggtgat cggtgccacg    1320
gtgatggagg gcttctacgt catcttcgac agagcccaga gagggtggg cttcgcagcg    1380
agccctgtg cagaaattgc aggtgctgca gtgtctgaaa tttccgggcc tttctcaaca    1440
gaggatgtag ccagcaactg tgtccccgct cagtctttga gcgagcccat tttgtggatt    1500
gtgtcctatg cgctcatgag cgtctgtgga gccatcctcc ttgtcttaat cgtcctgctg    1560
ctgctgccgt tccggtgtca gcgtcgcccc cgtgaccctg aggtcgtcaa tgatgagtcc    1620
tctctggtca gacatcgctg gaaatgaata gccaggcctg acctcaagca accatgaact    1680
cagctattaa gaaaatcaca tttccagggc agcagccggg atcgatggtg gcgctttctc    1740
ctgtgcccac ccgtcttcaa tctctgttct gctcccagat gccttctaga ttcactgtct    1800
tttgattctt gattttcaag ctttcaaatc ctccctactt ccaagaaaaa aaaaaaaaa    1860
aa                                                                   1862
```

<210> SEQ ID NO 2
<211> LENGTH: 518

<212> TYPE: PRT
<213> ORGANISM: HOMO SAPIENS

<400> SEQUENCE: 2

Met Gly Ala Leu Ala Arg Ala Leu Leu Pro Leu Leu Ala Gln Trp
1               5                   10                  15

Leu Leu Arg Ala Ala Pro Glu Leu Ala Pro Ala Pro Phe Thr Leu Pro
            20                  25                  30

Leu Arg Val Ala Ala Ala Thr Asn Arg Val Val Ala Pro Thr Pro Gly
        35                  40                  45

Pro Gly Thr Pro Ala Glu Arg His Ala Asp Gly Leu Ala Leu Ala Leu
50              55                  60

Glu Pro Ala Leu Ala Ser Pro Ala Gly Ala Ala Asn Phe Leu Ala Met
65                  70                  75                  80

Val Asp Asn Leu Gln Gly Asp Ser Gly Arg Gly Tyr Tyr Leu Glu Met
                85                  90                  95

Leu Ile Gly Thr Pro Pro Gln Lys Leu Gln Ile Leu Val Asp Thr Gly
                100                 105                 110

Ser Ser Asn Phe Ala Val Ala Gly Thr Pro His Ser Tyr Ile Asp Thr
            115                 120                 125

Tyr Phe Asp Thr Glu Arg Ser Ser Thr Tyr Arg Ser Lys Gly Phe Asp
        130                 135                 140

Val Thr Val Lys Tyr Thr Gln Gly Ser Trp Thr Gly Phe Val Gly Glu
145                 150                 155                 160

Asp Leu Val Thr Ile Pro Lys Gly Phe Asn Thr Ser Phe Leu Val Asn
                165                 170                 175

Ile Ala Thr Ile Phe Glu Ser Glu Asn Phe Phe Leu Pro Gly Ile Lys
                180                 185                 190

Trp Asn Gly Ile Leu Gly Leu Ala Tyr Ala Thr Leu Ala Lys Pro Ser
            195                 200                 205

Ser Ser Leu Glu Thr Phe Phe Asp Ser Leu Val Thr Gln Ala Asn Ile
210                 215                 220

Pro Asn Val Phe Ser Met Gln Met Cys Gly Ala Gly Leu Pro Val Ala
225                 230                 235                 240

Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
                260                 265                 270

Tyr Tyr Gln Ile Glu Ile Leu Lys Leu Glu Ile Gly Gly Gln Ser Leu
            275                 280                 285

Asn Leu Asp Cys Arg Glu Tyr Asn Ala Asp Lys Ala Ile Val Asp Ser
        290                 295                 300

Gly Thr Thr Leu Leu Arg Leu Pro Gln Lys Val Phe Asp Ala Val Val
305                 310                 315                 320

Glu Ala Val Ala Arg Ala Ser Leu Ile Pro Glu Phe Ser Asp Gly Phe
                325                 330                 335

Trp Thr Gly Ser Gln Leu Ala Cys Trp Thr Asn Ser Glu Thr Pro Trp
                340                 345                 350

Ser Tyr Phe Pro Lys Ile Ser Ile Tyr Leu Arg Asp Glu Asn Ser Ser
            355                 360                 365

Arg Ser Phe Arg Ile Thr Ile Leu Pro Gln Leu Tyr Ile Gln Pro Met
        370                 375                 380

Met Gly Ala Gly Leu Asn Tyr Glu Cys Tyr Arg Phe Gly Ile Ser Pro
385                 390                 395                 400

-continued

```
Ser Thr Asn Ala Leu Val Ile Gly Ala Thr Val Met Glu Gly Phe Tyr
            405                 410                 415

Val Ile Phe Asp Arg Ala Gln Lys Arg Val Gly Phe Ala Ala Ser Pro
            420                 425                 430

Cys Ala Glu Ile Ala Gly Ala Ala Val Ser Glu Ile Ser Gly Pro Phe
            435                 440                 445

Ser Thr Glu Asp Val Ala Ser Asn Cys Val Pro Ala Gln Ser Leu Ser
        450                 455                 460

Glu Pro Ile Leu Trp Ile Val Ser Tyr Ala Leu Met Ser Val Cys Gly
465                 470                 475                 480

Ala Ile Leu Leu Val Leu Ile Val Leu Leu Leu Pro Phe Arg Cys
            485                 490                 495

Gln Arg Arg Pro Arg Asp Pro Glu Val Val Asn Asp Glu Ser Ser Leu
            500                 505                 510

Val Arg His Arg Trp Lys
            515
```